(12) United States Patent
Hattendorf et al.

(10) Patent No.: US 7,976,854 B2
(45) Date of Patent: Jul. 12, 2011

(54) METHOD OF TREATING SKIN REQUIRING SKIN CANCER TREATMENT

(75) Inventors: Judy Hattendorf, Marina Del Ray, CA (US); Steve Carlson, San Mateo, CA (US)

(73) Assignee: OMP, Inc., Long Beach, CA (US)

( * ) Notice: Subject to any disclaimer, the term of this patent is extended or adjusted under 35 U.S.C. 154(b) by 561 days.

(21) Appl. No.: 11/648,333

(22) Filed: Dec. 29, 2006

(65) Prior Publication Data

US 2007/0154503 A1 Jul. 5, 2007

Related U.S. Application Data

(60) Provisional application No. 60/755,359, filed on Dec. 30, 2005.

(51) Int. Cl.
*A61K 8/31* (2006.01)
*A61K 8/36* (2006.01)

(52) U.S. Cl. .................... 424/401; 424/59; 514/725

(58) Field of Classification Search ............... 424/401
See application file for complete search history.

(56) References Cited

U.S. PATENT DOCUMENTS

| | | | |
|---|---|---|---|
| 2,376,884 A | 5/1945 | Schwenk et al. |
| 2,377,188 A | 5/1945 | Schwenk et al. |
| 3,755,560 A | 8/1973 | Dickert et al. |
| 3,856,934 A | 12/1974 | Kligman |
| 4,136,166 A | 1/1979 | Barnett et al. |
| 4,229,427 A | 10/1980 | Whitehouse |
| 4,421,769 A | 12/1983 | Dixon et al. |
| 4,466,955 A | 8/1984 | Calvo et al. |
| 4,526,779 A | 7/1985 | Hashimoto |
| 4,792,443 A | 12/1988 | Filomeno |
| 5,143,763 A | 9/1992 | Yamada et al. |
| 5,523,077 A | 6/1996 | Pawelek et al. |
| 5,621,006 A | 4/1997 | Yu et al. |
| 6,497,860 B1 | 12/2002 | Kawato et al. |
| 6,699,464 B1 | 3/2004 | Popp et al. |
| 2004/0052741 A1 | 3/2004 | Wortzman et al. |
| 2004/0185016 A1 | 9/2004 | Popp et al. |
| 2006/0251598 A1* | 11/2006 | Ramirez et al. ............ 424/70.1 |

FOREIGN PATENT DOCUMENTS

EP 0 688 204 B1 12/1995
WO WO 01/85102 A2 11/2001

OTHER PUBLICATIONS

Contemplating Cosmetic Procedures, Article dated 2003, http://web.archive.org/web/20031203005324/www.obagi.com/heal/heal__main__frm.html, accessed May 8, 2008 using the Wayback Machine (http://www.archive.org/index.php).*
Obagi Nu-Derm(R) System Physician Prescribing Information Sheet, Revised Aug. 2003.*
Nguyen et al. ("Nonmelanoma Skin Cancer" Current Treatment Options in Oncology, 2002, 3, 193-203.).*
1995 U.S. Pharmacopeia/National Formulary USP 23/NF 18, pp. 769-770 and 1572-1573.
*Cosmetic/Personal Care Packaging. Containers.* http://www.cpcpkg.com, Oct. 22, 2004.
Tina S. Alster, "Combined Laser Resurfacing and Tretinoin Treatment of Facial Rhytides", *Cosmetic Dermatology*, vol. 10, No. 11, pp. 39-42 (Nov. 1997).
Nicholas Lowe, "Understanding How Topical Retinoids Work", *Skin & Aging*, pp. 39-42 (Feb. 1999).
Olsen, et al. "Tretinoin Emollient Cream for Photodamaged Skin: Results of 48-Week, Multicenter, Double-Blind Studies", *Journal of the American Academy of Dermatology*, pp. 217-226 (Aug. 1997).
Green, et al. "Photoaging and the Skin", *Dermatologic Clinics*, vol. 11, No. 1 pp. 97-105 (Jan. 1993).
Buka et al. "How to use Retinoids To Prevent Skin Cancer and Treat Photoaging", *Skin & Aging*, pp. 32-39 (Jun. 1999).
Brochure—The Science of Skin Health Restoration—Nu-Derm System (2000).
Insert, Obagi Medical Products, Inc., Long Beach, CA 90502 (2000).

* cited by examiner

*Primary Examiner* — Sharmila G. Landau
*Assistant Examiner* — Kortney L Klinkel
(74) *Attorney, Agent, or Firm* — Carter, DeLuca, Farrell & Schmidt, LLP

(57) ABSTRACT

A treatment regimen for treating skin subject to skin cancer treatments involves the application of supplemental composition(s) such as preparatory composition(s), protective composition(s), and combinations thereof, and a corrective composition.

21 Claims, No Drawings

METHOD OF TREATING SKIN REQUIRING SKIN CANCER TREATMENT

CROSS REFERENCE TO RELATED APPLICATION

This Application claims priority benefit of U.S. Provisional Application No. 60/755,359 filed Dec. 30, 2005 the entire disclosure of which is incorporated herein by this reference.

BACKGROUND

1. Technical Field

This disclosure relates to the sequential topical application of compositions in a prescribed fashion to enhance the results of a skin cancer treatment and minimize the adverse effects of the treatment. The disclosure further relates to the pre and post application of corrective compositions and one or more supplementary compositions to skin in association with skin cancer treatment. Kits containing corrective compositions and supplementary compositions for use in connection with skin cancer treatment are also described.

2. Background of Related Art

Over one million cases of nonmelanoma skin cancer are diagnosed in the United States each year. Current treatment options for skin cancer treatment include a variety of lasers, dermabrasion, salabrasion, surgical excision, and cryotherapy. Although some treatments may be effective, they may be expensive, time consuming, and painful. In some cases, such treatments also may result in cosmetically undesirable scarring.

Thus, there remains room for improvement in skin cancer treatment techniques, and especially to minimize, reduce, or eliminate the undesirable side effects and/or the need for multiple treatments.

SUMMARY

Skin requiring skin cancer treatment is pre-treated in accordance with the present disclosure by preconditioning skin by the sequential topical application of one or more corrective compositions, and one or more supplementary compositions in a morning regimen; followed by the sequential topical application of one or more corrective compositions, including tretinoin, and one or more supplementary compositions in an evening regimen. Such preconditioning by the sequential application of such compositions may minimize, reduce, or eliminate the undesirable side effects and/or the need for multiple skin cancer treatment treatments.

Optionally, after a skin cancer treatment is performed on the preconditioned skin, the skin may be post-treated by another sequential topical application of one or more corrective compositions, and one or more supplementary compositions in a morning regimen; followed by the sequential topical application of one or more corrective compositions, including tretinoin, and one or more supplementary compositions in an evening regimen. Post-treatment of preconditioned skin may minimize, reduce, or eliminate the undesirable side effects of skin cancer treatment such as reactions or complications like post-inflammatory hyperpigmentation, erythema (redness), acne and scarring. Post-treatment may also reduce the need for multiple skin cancer treatments.

In addition, dermatological treatment regimens in accordance with the present disclosure may improve characteristics of a user's skin. The regimens include the application of one or more corrective compositions and the application of one or more supplementary compositions. Suitable corrective compositions include, for example, compositions which help to repair damage to the deeper layers of skin, or stable corrective compositions which contain one or more active ingredients sensitive to oxidation that remain stable for three years at room temperature. Suitable supplementary compositions include, for example: preparatory compositions which make skin more receptive to the corrective compositions; or protective compositions which further protect skin against damage from harmful UVA and UVB rays. Depending on the nature of the one or more supplementary compositions, they may be applied before, after, or both before and after application of the corrective composition.

In embodiments, the present disclosure is directed towards kits for pre-treating and post-treating skin subject to a skin cancer treatment containing both one or more stable corrective compositions and one or more supplementary compositions.

These and other aspects of this disclosure will be evident upon reference to the following detailed description.

DETAILED DESCRIPTION OF PREFERRED EMBODIMENTS

Treatment regimens in accordance with this disclosure include the sequential steps of: pre-treating the surface of skin in need of a skin cancer treatment; performing a skin cancer treatment; and optionally post-treating the skin. The pre-treatment and post-treatment may include the sequential topical application of treatment compositions in a prescribed fashion.

The first step of the present method is pre-treatment. The pre-treatment step of the treatment regimen of the present disclosure is designed for pre-conditioning the skin to rendering the area of skin to be treated more receptive and responsive to a skin cancer treatment. For example, skin that is oily or dirty can be preconditioned to a healthier more hygienic state. It has been found that preconditioning skin by cleaning, toning, exfoliating, and/or using corrective compositions in accordance with the present disclosure may reduce adverse effects of a skin cancer treatment. Moreover, the sequential topical application of treatment compositions in accordance with the present disclosure may contribute to skin cancer treatments by providing excellent aesthetic results with reduced recovery periods, while markedly improving rejuvenation goals and aesthetic expectations.

Thus, skin in need of skin cancer treatment is pre-treated by preconditioning skin by the sequential topical application of one or more corrective compositions, and one or more supplementary compositions in a morning regimen; followed by the sequential topical application of one or more corrective compositions, including tretinoin, and one or more supplementary compositions in an evening regimen.

As used herein the word "treat," "treating" or "treatment" refers to using the compositions of the present disclosure prophylactically to prevent outbreaks of undesirable dermatological symptoms, or therapeutically to ameliorate an existing undesirable dermatological condition, and/or extend the duration of the aesthetic benefit of a skin cancer treatment, or reduce the frequency of repeated skin cancer treatments.

Pre-treatment regimens in accordance with the present disclosure improve skin characteristics through sequential application of pre-selected skin care compositions to the skin of a user prior to the skin cancer treatment. As used herein the word "corrective composition" refers to using the compositions of the present disclosure which have an active ingredient for treating any undesirable dermatological condition. Application of the corrective composition in combination with the one or more supplementary compositions provides improved effectiveness of the corrective composition compared to application of the corrective composition alone. As used herein the word "supplementary composition" refers to using compositions of the present disclosure which do not have active ingredient for treating undesirable dermatological conditions, however when used in conjunction with a corrective composition produce a beneficial effect.

The supplementary composition can be, for example, a preparatory composition that makes the skin of the user more receptive to the corrective composition. Alternatively, the supplementary composition may be a protective composition that protects skin against damage from harmful UVA and UVB rays.

Depending on the exact nature of the supplementary compositions employed, the supplementary composition may be applied before or after application of the corrective composition. For example, where the supplementary composition is a preparatory composition, the supplementary composition is applied before the corrective composition. Where the supplementary composition is a protective composition, the supplementary composition is applied after the corrective composition. In particularly useful embodiments, one or more supplementary compositions can advantageously be applied both before and after application of the corrective composition.

In embodiments, pre-treatment regimens in accordance with the present disclosure include a first treatment, such as in the morning hours, and a second treatment, such as in the evening hours. Both the first and second treatments include the topical application of one or more corrective compositions, along with one or more supplemental compositions. It should, of course be understood that the supplementary compositions used in the first treatment can be different from the supplementary compositions applied in the second treatment. Likewise, it should be understood that the corrective compositions used in the first treatment can be different from the corrective compositions applied in the second treatment.

In embodiments, the first treatment occurs in the morning hours and includes the application of an effective amount of one or more preparatory compositions (e.g., foaming gel, and toner) followed by application of an effective amount of one or more corrective compositions (e.g., exfoliator, and/or one or more hydroquinone compositions) followed by the application of an effective amount of one or more protective compositions (e.g., sun protector). In this embodiment, the second treatment occurs in the evening hours and includes the topical application of an effective amount of one or more preparatory compositions (e.g., foaming gel, and toner) followed by application of an effective amount of one or more corrective compositions (e.g., hydroquinone and tretinoin compositions). In embodiments, tretinoin is used either alone or in combination with other corrective compositions during the evening treatment.

Materials suitable for use as pre-treatment composition include corrective compositions and supplementary compositions pre-selected to clean, tone, exfoliate, treat or precondition skin in need of a skin cancer treatment. Non-limiting examples of pre-treatment compositions are listed below and include supplementary compositions such as cleanser compositions, toner compositions, and exfoliant compositions. Other suitable pre-treatment compositions include corrective compositions such as stable corrective compositions and stimulating corrective compositions. The pre-treatment compositions are categorized in various classes however this classification is not intended to limit the pre-treatment compositions in any way to only to those pre-treatment compositions belonging to the categories herein mentioned. Moreover, as described below, the same or different pre-treatment compositions can be used as post-treatment compositions in accordance with the present disclosure. In embodiments, OBAGI NU-DERM® brand skin care products available from OMP, Inc. of Long Beach, Calif. may be suitable for use as pre-treatment and/or post-treatment compositions. OBAGI NU-DERM® brand skin care products include a variety of compositions such as those described above. Products include, for example, skin creams, exfoliating creams, clarifiers, sun blocks, lotions, cleaning creams and lotions, skin lighteners, toners, and moisturizers.

Supplementary Compositions

Non-limiting examples of supplementary compositions which may be combined with the corrective compositions of this disclosure are listed below.

Suitable supplementary compositions are categorized in various classes (e.g. preparatory compositions and protective compositions) however this classification is not intended to limit the supplemental compositions in any way to only those compositions belonging to the categories herein mentioned.

Preparatory Compositions

Throughout the pre-treatment regimen of the present disclosure, skin improvement may be slowed or worsened by skin becoming dirty or oily throughout the day and night. Dirt and oil clog pores and slow the corrective compositions from contacting the inner layers of skin. One class of supplementary compositions that may be combined with the corrective compositions of the present disclosure is preparatory compositions which make skin more receptive to the corrective step.

Thus, the pre-treatment regiment of the present disclosure includes the step of preparing skin to make it more receptive to the corrective step by applying preparatory compositions. Suitable preparatory compositions include cleansers, foaming gels, toners, and combinations thereof, which may be applied to the skin in the morning or evening portion of the treatment regimen.

The cleanser is applied to skin in amounts that provide the benefit to the skin of the user, such as in an amount sufficient to remove dirt and oil from the skin. Generally, the cleansers are soap-free and include water, detergent, surfactant, humectants, skin conditioning agent, PH adjustor, extracts, preservatives, fragrance and colorant, however, any cleaner suitable for removing dirt and oil from skin may be used. One commercially available cleanser is OBAGI NU-DERM® brand gentle cleanser available from OMP, Inc. of Long Beach, Calif. The OBAGI NU-DERM® gentle cleanser contains a combination of water, cocamidopropyl betaine, sodium lauroyl oat amino acids, sodium laureth sulfate, glycerin, aloe barbadensis gel, glycerth-7, apricot triethanolamine, sage extract, borage extract, phenoxyethanol, methylparaben, propylparaben, ethylparaben, butylparaben, saponins, fragrance, and colorant.

Optionally, a foaming gel may be applied as one of the preparatory compositions in amounts that provide the benefit to the skin of the user, such as in an amount sufficient to remove dirt, oil and/or impurities to clean skin and leave it more receptive to treatment. Generally, foaming gels include water, detergent, surfactant, humectants, skin conditioning agent, PH adjustor, extracts, preservatives, fragrance and colorant, however any foaming gel may be applied that cleans the skin by removing dirt and/or oil. One commercially available foaming gel is OBAGI NU-DERM® brand foaming gel available from OMP, Inc. of Long Beach, Calif. The OBAGI NU-DERM® foaming gel contains a combination of water, sodium lauryl oat amino acids, cocamidopropyl betaine, sodium laureth sulfate, aloe barbadensis gel, alfalfa extract, borage extract, sodium chloride, xantham gum, saponins, phenoxythanol, methylparaben, propylparaben, ethylparaben, butylparaben, fragrance and colorant.

Optionally, toner may be applied as a preparatory composition in amounts that provide the benefit to the skin of the user, such as in an amount sufficient to hydrate and tone skin while reducing the pH. Toner also may help remove dirt, oils, and grime without overly drying out sensitive skin. Generally, toners include water, skin conditioner, astringent, minerals, moistening agent, vitamins and complexes thereof, anti-microbial, cleanser, extract, surfactant, anti-irritant, fragrance and colorant; however any commercially available skin toner may be used. One commercially available toner is OBAGI NU-DERM® brand toner available from OMP, Inc. of Long Beach, Calif. The OBAGI NU-DERM® toner contains a combination of water, aloe barbadensis gel, witch hazel distillate, potassium alum, sodium PCA, panthenol, DMDM hydantion, polysorbate 80, allantoin, sage extract, calendula officinalis extract, saponins, fragrance, and colorant.

During the treatment regimen, the preparatory composition(s) can advantageously be applied to damp skin of the face and neck with moistened fingertips. The face and neck of the user can be rinsed with warm water after application of the preparatory composition(s).

Protective Compositions

Skin improvement may be slowed or worsened by sunrays which may cause pigmentation and dryness. Accordingly, protective compositions are one class of supplementary compositions that optionally may be combined with the corrective compositions in the treatment regimens of the present disclosure to alleviate sun damage or dryness.

Suitable protective compositions include any composition capable of reducing skin damage, darkening, or dryness. In embodiments, protective compositions include sun block to screen out ultraviolet light rays. In embodiments, suitable protective compositions include creams are moisturizers formulated to help control dryness.

One suitable commercially available protective composition is OBAGI NU-DERM® brand Sunblock, from OMP, Inc. of Long Beach, Calif. This protective composition provides broad-spectrum sun protection and can advantageously be applied every morning as part of a treatment regimen in accordance with this disclosure. The formulation is made of octinoxate, zinc oxide, butylparaben, cetearyl alcohol, citric acid, C13-14 isoparaffin, diethanolamine cetyl phosphate, disodium edetate, ethylparaben, isobutylparaben, isopropyl palmitate, laureth-7, methylparaben, octyl stearate, phenoxyethanol, polyacrylamide, polyether-1, polysorbate 60, propylparaben, purified water, sodium hydroxide, and triethoxycaprylylsilane.

Another suitable commercially available protective composition is a sunblock available as OBAGI NU-DERM® Physical UV Block SPF 32. This composition contains zinc oxide USP, beeswax, butylene glycol, cetyl dimethicone, cetyl PEG/PPG-10/1 dimethicone, dimethicone, disodium EDTA, glycereth-26, hydrogenated castor oil, isopropyl palmitate, methylparaben, octyl stearate, propylparaben, purified water, sodium propylparaben, purified water, sodium chloride, triethoxycaprlylsilane, tocopherol acetate, and willowherb extract.

Other suitable commercially available protective compositions include sunscreens such as OBAGI NU-DERM® Healthy Skin Protection (SPF 35) and eye creams such as OBAGI NU-DERM® brand Eye Cream.

Corrective Compositions

Non-limiting examples of corrective compositions which may be combined with the supplementary compositions of this disclosure are listed below.

Suitable corrective compositions are categorized in various classes (e.g. stimulating corrective compositions and stable protective compositions) however this classification is not intended to limit the corrective compositions in any way to only those compositions belonging to the categories herein mentioned. In fact, where necessary all ingredients used in the stable corrective compositions may be utilized to make the stimulating corrective compositions regardless of stability achieved.

Stimulating Corrective Compositions

Throughout the treatment regimen of the present disclosure, skin may be, among other things, regenerated by contacting the skin with one or more stimulating corrective compositions. Such compounds include those capable of the gradual bleaching of hyper-pigmented skin conditions such as chloasma melasma, freckles, sensile lentigines, and other unwanted areas of melanin hyper-pigmentation. Thus, suitable stimulating corrective compositions include, but are not limited to compositions having one or more active ingredients which help to repair damage to the deeper layers of skin, such as skin blending compositions, hydroquinone compositions, retinoid compositions, tretinoin compositions, retin-A compositions, and combinations thereof.

The corrective compositions can be applied to the skin in amounts that provide the benefit to the skin of the user, such as in an amount sufficient to repair damage to the deeper layers of skin. Typically corrective compositions are applied to the skin in the two treatments per day, such as a morning (a.m.) and evening (p.m.) treatment. It should of course be understood that applying corrective compositions in one treatment is also possible, especially where the active ingredient is potent, such as tretinoin.

One corrective composition is a blending composition which promotes pigmentation correction at the cellular level promoting even skin color. Generally blending compositions include skin lightening agent such as hydroquinone, preservative, chelating agent, emulsifier, humectant, pH adjuster, antioxidant, emollient, reducing agent and water. Moreover, blending compositions with improved stability as those described below may also be used for correcting the skin in accordance with this disclosure.

One commercially available blending composition is OBAGI NU-DERM®BLENDER® available from OMP, Inc. of Long Beach, Calif. The OBAGI NU-DERM® BLENDER® composition contains a combination of hydroquinone USP 40 mg/gm in a base of purified water, glycerin, cetyl alcohol, PPG-2 myristyl ether propionate, sodium lauryl sulfate, TEA-salicylate, lactic acid, phenyl trimethicone, tocopheryl acetate, sodiummetabisulfite, ascorbic acid, methylparaben, saponins, disodium EDTA, BHT and propylparaben.

Other suitable corrective compositions include retinoid containing compositions applied in amounts sufficient to provide benefit to the skin, such as medically prescribed tretinoin. Tretinoin skin preparations are a family of drugs all similar to Vitamin A available in gel or cream form. Tretinoin can advantageously be used in combination with alpha hydroxyacid preparations. The inclusion of a tretinoin corrective composition in the present treatment regimen may aid in keratinocyte activity regulation, mitosis, repairing damaged DNA, blood vessel formation such as angiogenesis, and the creation of a soft epidermis.

The incorporation of retinoid containing corrective composition into the sequential treatment regimen of the present disclosure can promote a smoother less wrinkled skin and can be effective in treating sun damage, wrinkling, hyperpigmentation and facial roughness. Although not wishing to be bound by this disclosure, it is believed that tretinoin passes through the skin cell membranes to the nucleus wherein it binds to nuclear receptors and regulates transcription of genes that mediate the rate of cell division and turnover, cell differentiation and formulation of new healthy collagen and the repair of elastin. As a result skin can be firmer from the collagen formation as well as more flexible from the repair of elastin.

Tretinoin also increases the formation of normal keratinocytes (cells making up about 90% of the epidermis) and fibroblasts (connective tissue cells which secrete an extracellular matrix rich in collagen and other macromolecules), decreases melanocyte activity (which offers better resistance to external injury and inflammation) and is found to improve angiogenesis (the formation of new blood vessels that increase skin circulation).

Suitable tretinoin compositions for use with the treatment regimen of the present disclosure utilize a medically prescribed tretinoin medication such as, 0.05 and 0.1 Tretinoin (generic). Suitable tretinoin compositions are commercially available under a variety of trade names. In embodiments, the retinoid containing stimulating composition used in the treatment regimen of the present disclosure is an oil-in-water emulsion, such as commercially available tretinoin creams containing 0.05% or 0.1% actives.

Another suitable corrective composition is a skin lightener with sunscreen available as OBAGI NU-DERM® SUN-FADER®, from OMP, Inc. of Long Beach, Calif. Each gram of OBAGI NU-DERM® SUNFADER® composition contains hydroquinone, octinoxate, and oxybenzone 5.5% in a base of purified water, cetyl alcohol, glycerin, sodium lauryl sulfate, stearyl alcohol, tocopheryl acetate, ascorbic acid, sodium metabisfulfite, disodium EDTA, methylparaben, saponins, propylparben, BHT and butylparaben.

Another suitable commercially available corrective composition is hydroquinone compositions available as OBAGI NU-DERM® Clear from OMP, Inc. of Long beach, CA. One gram of OBAGI NU-DERM® Clear composition contains hydroquinone in a base of purified water, cetyl alcohol, glycerin, sodium lauryl sulfate, stearyl alcohol, tocopheryl acetate, ascorbic acid, sodium metabisulfite, lactic acid, saponins, disodium EDTA, methylparaben, BHT, propylparaben and butylparaben.

Other corrective compositions include exfoliating lotion to smooth and tone rough or damaged skin. Suitable exfoliators include OBAGI NU-DERM® EXFODERM® and OBAGI NU-DERM® EXFODERM® Forte. OBAGI NU-DERM® EXFODERM® exfoliator typically contains water, ethoxydiglycol, phytic acid, glycerin, cetearyl alcohol, glyceryl stearate, PEG-100 stearate, canola oil, isohexadecane, magnesium aluminum silicate, potassium cetyl phosphate, cetyl alcohol, bis-diglyceryl polyacyladipate-2, dimethicone, polysorbate 0, PEG-150 stearate, steareth-20, xanthan gum, glycereth-7, tocopheryl acetate, saponins, phenoxyethanol, methylparaben, propylparaben, butyparaben, ethylparaben, isobutylparaben. OBAGI NU-DERM® EXFODERM® Forte exfoliator typically contains purified water, glycolic acid, emulsifying wax, triethanolamine, glycerin, lactic acid, caprylic/capric triglyceride, kalaya oil, stearic acid, cetyl alcohol, dimethicone, methylparaben, propylparaben, saponins.

Stable Corrective Compositions

In any topical treatment regimen, instability of the topical composition containing the active may cause degradation of the active requiring application of unnecessarily large amounts of the active ingredient and of potentially irritating degradation by-products to the skin. It has been found that these problems can be eliminated or reduced by the use of corrective composition having three years of stability at room temperature.

Accordingly, in embodiments the present disclosure relates to stable active containing corrective compositions. These stable corrective compositions can be made, for example, by the methodology described in this disclosure copending application Ser. No. 11/291,400, the entire disclosure of which is incorporated herein by this reference; however, any method of making the corrective compositions may be employed so long as they achieve the desired stability. Thus, the stable corrective compositions are formulated, manufactured and packaged in accordance with this disclosure in a manner which enables the composition to remain in the package without discoloring. As used herein the term "stable" means that the composition when in a closed container remains within the tolerances and limits set forth in US Pharmacopeia and/or the US FDA guidelines or monographs for compositions containing any particular active ingredient or combination of active ingredients. The entire US Pharmacopeia and collection of US FDA guidelines or monographs for compositions containing any particular active ingredient or combination of active ingredients are too voluminous to present in their entirety herein and thus are instead incorporated in their entirety by this reference. With respect to topical compositions, the tolerances and limits are frequently presented relative to the labeled amount. As one illustrative example, for hydroquinone cream, the acceptable tolerance is not less than 94.0 percent and not more than 106.0 percent of the labeled amount of $C_6H_6O_2$. As another illustrative example, for tretinoin cream, the acceptable tolerance is not less than 90.0 percent and not more than 130.0 percent of the labeled amount of $C_{20}H_{28}O_2$. Those skilled in the art will readily be able to identify the tolerances and limits for other compositions containing other active ingredients.

As those skilled in the art will appreciate, the container-liner-closure system used to store the composition will affect the stability of the active ingredient. It should be understood that a composition need not be stable in all containers to be stable in accordance with this disclosure. Stability in at least one type of container is sufficient for a composition to be stable as that term is used herein.

In embodiments, stable corrective compositions in accordance with the present disclosure can be stable for at least three years at room temperature. Stability of the present compositions can be evaluated through accelerated stability studies. In these studies, the packaged composition is maintained at an elevated temperature for a period of time after which it is examined. The exposure to elevated temperatures for a given period correlates to a correspondingly longer period of time at room temperature. Thus, for example, if a product remains within the required tolerances and limits when maintained for a period of 12 weeks at a temperature of 40° C. and 12 months further at room temperature, one can conclude that the product has a shelf life of greater than two and up to three years at room temperature. Those skilled in the art will envision other testing to confirm the stability of the products described herein.

Skin Cancer Treatment Techniques

The second step of the present methods is performing a skin cancer treatment on preconditioned skin. Any skin cancer treatment may be employed. Suitable skin cancer treatments are within the purview of those skilled in the art. Illustrative, non-limiting examples of treatments available for skin cancer are described below. The ideal treatment should be one that most effectively eradicates the cancer, maximally spares normal skin, is painless, without side effects, and heals rapidly with minimal scarring. Each patient and individual skin cancer(s) may demonstrate different features that make one of the above treatments more effective than the others. The best treatment is one that is selected, by the patient and physician, after reaching a complete understanding of the available therapeutic modalities.

Electrodessication and curettage is a very common procedure used in the treatment of basal cell carcinomas that are generally of small size and located in low recurrence areas of the body (neck, trunk, extremities). The area is first numbed with a local anesthetic injection and then scraped from surrounding normal skin with a curette (a circular, sharp instrument). An electrosurgical needle is then used to desiccate (heat and dry up) the remaining cancerous tissue. This is repeated for a total of three or four times in succession in order to achieve maximal cure rates. This form of treatment is quick, efficient and cost effective. It is limited however, by leading to higher recurrence rates when treating large lesions and cancers of the mid face. Pain during treatment is minimal and post-operatively the area may feel comparable to a small burn. The cosmetic result will appear as a lighter (hypopigmented) flat spot that is of similar size as the cancer was prior to treatment. The method requires no stitches, only one post operative visit (usually) and is healed with 10-21 days.

Cryosurgery is a term given to a procedure that involves the application of a very cold substance in order to destroy tissue. To achieve tumor killing, a tissue temperature of −50° C. is required. In dermatology, the most frequently used cryosurgical substance is liquid nitrogen (−196° C.), which is applied using a pressurized canister. No anesthesia is necessary for small tumors and the application of the freezing spray is felt as a burning sensation. With larger tumors, anesthetics may be used as may temperature measuring devices in order to monitor the extent of freezing within the cancer.

Laser Vaporization involves the use of the carbon dioxide laser to vaporize away abnormal tissue after the area has been anaesthetized. It may be combined with curettage and is particularly useful in cases of multiple/superficial tumors.

Surgical excision is a technique that involves the use of a scalpel to excise (cut out) the cancerous tissue. The area of the cancer is numbed using a local anesthetic, and a small measurement of 2-4 mm of normal skin surrounding the lesion is made. The cancer plus surrounding normal skin is then removed by incision with the scalpel blade. Stitches are placed to bring the adjacent wound edges together. In some cases, extra skin may be mobilized or taken from a distant site, in order to cover the surgical defect (flap or graft). Pain during treatment is minimal and post-operatively, may feel comparable to that of a bruise. Surgical excision may require 1-2 post operative visits (including suture removal), and heals more rapidly than that of ED&C and cryosurgery. The cosmetic result is superior to the previously mentioned techniques, but is dependent upon the size and location of the tumor.

Micrographic (Moh's) Surgery is a microscopically guided method of tracing and removing basal cell carcinomas. The procedure is a form of surgical excision that has been modified with mapping the margins of the tissue specimen to determine whether tumor remains. This technique spares normal tissue because of the microscopic control involved. The pain, post-operative cosmetic result, follow up care, and healing time are similar as with standard surgical excision. The Radiation therapy, or x-ray therapy, can also be used in the treatment of certain basal cell carcinomas in some patients. Radiation therapy techniques are within the purview of those skilled in the art.

Topical 5-fluorouracil (5-FU) is a topical chemotherapy agent used commonly to treat precancerous lesions known as actinic or solar keratoses. With regard to the treatment of true cancers, it is only effective for the superficial type basal cell carcinomas. It is usually applied twice daily for 6-12 weeks but the exact regime may vary according to the patients needs, and works by destroying the actively growing cancer cells.

Photodynamic therapy (PDT) is a promising non-surgical technique that involves the systemic or topical application of a photosensitizing drug that is preferentially retained in tumors, and with exposure to light of the correct wavelength, results in selective destruction of cancerous cells. Initial studies with PDT show good cure rates and excellent cosmetic results for superficial tumours.

The skin cancer treatment step will typically be performed in accordance with techniques known in the art by a physician.

Post-Treatment

Optionally, the treatment regimen can include post-treating the pre-conditioned/treated skin. Typically, the type of skin cancer treatment performed on the skin treatment area will dictate the type of post-treatment compositions to be applied. For example, the procedure can be varied depending on the apparatus used by the dermatologist in performing the skin cancer treatment. Furthermore, the post-treatment can include repeating the pre-treatment steps described above with the same or different pre-treatment compositions including any supplementary compositions and corrective compositions described above.

It should be noted that post-treatment can comprise not just a single application of a single corrective or supplementary composition but can be a sequentially applied treatment. For example, multiple supplementary compositions can be used as well as multiple corrective compositions. Thus the classification as a post-treatment composition is not intended to limit the post-treatment compositions in any way to only those post treatment compositions mentioned herein.

In embodiments, after treating the preconditioned skin with a skin cancer treatment, skin is post-treated by another sequential topical application of one or more corrective compositions, and one or more supplementary compositions in a morning regimen; followed by the sequential topical application of one or more corrective compositions, including tretinoin, and one or more supplementary compositions in an evening regimen. Post-treatment of preconditioned skin enhances the benefits of the skin cancer treatment by limiting adverse events associated with skin cancer treatments.

In embodiments, the first post-treatment occurs in the morning hours and includes the application of an effective amount of one or more preparatory compositions (e.g., gentle cleanser, and toner) followed by application of an effective amount of one or more corrective compositions (e.g., exfoliating creams such as OBAGI NU-DERM® EXFODERM®, and/or one or more hydroquinone compositions such as OBAGI NU-DERM® Clear) followed by the application of an effective amount of one or more protective compositions (e.g., sun blocks such as OBAGI NU-DERM® UV Physical block). Note that where a skin cancer treatment has caused injury or removal of the epidermis, the application of exfoliant may advantageously be delayed until skin has re-epithelialized (or redness has greatly subsided). In embodiments, the second treatment occurs in the evening hours and includes the topical application of an effective amount of one or more preparatory compositions (e.g., gentle cleanser, and toner) followed by application of an effective amount of one or more corrective compositions (e.g., hydroquinone and tretinoin compositions). In embodiments, tretinoin is used either alone or in combination with other corrective compositions during the evening treatment.

Kit Components

As the pre-procedure treatment regimen requires the sequential application of various components, it has also been found that kits greatly facilitate the user in performing the pre-treatment regimen consistently. One suitable kit for pre-treatment includes the following:

---
Foaming Gel
Toner
OBAGI NU-DERM ® Clear
OBAGI NU-DERM ® BLENDER ®
OBAGI NU-DERM ® SUNFADER ®
Tretinoin (0.1% or 0.05%)
---

As the treatment regimen requires the sequential application of various post procedure components, it has also been found that kits greatly facilitate the user in performing the post-treatment regimen consistently. One suitable kit for post-treatment includes the following:

---
Foaming Gel
Toner
OBAGI NU-DERM ® Clear
OBAGI NU-DERM ® BLENDER ®
OBAGI NU-DERM ® SUNFADER ®
Tretinoin (0.1%-0.05%)
---

Typically, kits are provided with instructions for care. For example, the instructions may direct that the corrective and supplemental compositions of the pre-procedure treatment regimen be applied as follows:

| Pre-Treatment Regimen for Skin cancer treatment | Product | First Application (a.m.) | Second Application (p.m.) |
|---|---|---|---|
| Apply nickel size amount of preparatory composition to tumor and surrounding skin, then wash off. | Foaming Gel<br>Toner | X<br>X | X<br>X |
| Apply large pea size amount of corrective composition to tumor and surrounding skin. | OBAGI NU-DERM ® Clear<br>OBAGI NU-DERM ® BLENDER<br>Tretinoin | X<br>X | X<br>X<br>X |
| Apply pea size amount of protective composition to tumor and surrounding skin. | Sun screen or sun block | X | |

The instructions may also, in embodiments, direct that the corrective and supplemental compositions of the post-treatment regimen be applied as follows:

| Post-treatment Regimen for Skin cancer treatment | Product | First Application (a.m.) | Second Application (p.m.) |
|---|---|---|---|
| Apply pea size amount of preparatory composition to tumor and surrounding skin, then wash off. | Cleanser<br>Toner | X<br>X | X<br>X |
| Apply large pea size amount of corrective composition to tumor and surrounding skin. | OBAGI NU-DERM ® Clear<br>OBAGI NU-DERM ® BLENDER<br>Tretinoin | X | X<br>X<br>X |
| Apply pea size amount of protective composition to tumor and surrounding skin. Reapply as needed. | OBAGI NU-DERM ® SUNFADER ® | X | |

These instructions are illustrative. Those skilled in the art may readily envision other instructions. The second application may be performed at least four hours after the first treatment for both the pre-treatment and the post-treatment.

In embodiments, a patient follows a prescribed treatment regimen twice a day (in the morning and at night) for up to about nine weeks prior to undergoing a skin cancer treatment, preferably from about one to about seven weeks prior to undergoing a skin cancer treatment, most preferably from about three to about four weeks prior to undergoing a skin cancer treatment. The pre-treatment regimen involves applying designated skin care products from the commercially available OBAGI NU-DERM® system and/or prescription product in the smallest possible amount sufficient to cover at least the site intended for the skin cancer treatment, in embodiments, the entire face of the patient even if only a small area of the face is to receive the skin cancer treatment. The regimen may advantageously be as follows:

| | Morning | Evening |
|---|---|---|
| Prepare | Foaming Gel<br>Toner | Foaming Gel<br>Toner |
| Correct | OBAGI NU-DERM ® Clear<br>4% Hydroquinone 1 gm | OBAGI NU-DERM ® Clear<br>4% Hydroquinone 1 gm |
| Stimulate | | Tretinoin 0.05%<br>BLENDER ® 4% HQ 0.5 gm |
| Protect | SUNFADER ® | |

After the desired pre-treatment period, a skin cancer treatment is performed. After ensuring that sufficient re-epithelialization occurs, the patient resumes treatment with the previously used treatment regimen for a post-treatment time of up to about eleven weeks, preferably about one to about nine weeks, most preferably from about four to about six weeks.

Benefits of Pre-Treatment and Optional Post-treatment

The use of the presently described methods may provide one or more benefits to the skin of the user undergoing skin cancer treatments. For example, by employing the methods described herein, a patient undergoing skin cancer treatments may observe perioral fine wrinkle improvement, periocular fine wrinkle improvement, hyperpigmentation improvement, hypopigmentation improvement, tactile roughness improvement, sallowness improvement, acne scarring improvement and/or increased overall skin quality. Additionally, a patient undergoing skin cancer treatments employing the methods described herein may observe no worsening of Erythema.

In order that those skilled in the art may be better able to practice the compositions and methods described herein, the following non-limiting examples are given for illustration purposes.

Example 1

A 34 year old white female in good general health is presented to dermatologist requesting removal of a tumor from her arm. The patient has little sun damage and indicates the desire to minimize, reduce, or eliminate the side effects of the skin cancer treatment process.

Pre-treatment:

The patient is started on a pre-treatment protocol to precondition her skin in preparation for the upcoming skin cancer treatment.

The patient is prescribed tretinoin (0.05% or 0.1%) and provided with a pre-treatment kit containing a container of foaming gel, toner, OBAGI NU-DERM® Clear formulation, OBAGI NU-DERM® Sunfader® formulation, OBAGI NU-DERM® BLENDER®, and prescribed tretinoin. Each container provides enough formulation in an amount sufficient to be applied to the arm as instructed below for between 3 to 6 weeks prior to the skin cancer treatment.

Each kit contains instructions for the patient to apply the pre-treatment compositions every morning. The instructions require the following steps to be followed in the morning in sequential order: 1) apply a nickel-sized amount of foaming gel to wet skin, massage into the arm and rinse thoroughly; 2) apply toner using cotton pads or fingertips to entire arm; 3) apply 0.5 grams of OBAGI NU-DERM® Clear to the arm; and 4) apply OBAGI NU-DERM®SUNFADER® to the arm (Application of the protective composition can be repeated after 2 hours if patient is in direct sunlight).

The instructions further require the following steps to be followed in the evening in sequential order: 1) apply a nickel-sized amount of foaming gel to wet skin, massage into the arm and rinse thoroughly; 2) apply toner using cotton pads or fingertips to the arm; 3) apply 0.5 grams of OBAGI NU-DERM® Clear to the arm; 4) apply OBAGI NU-DERM® BLENDER® (0.5 grams) and tretinoin (0.5 grams). Apply in the evening after OBAGI NU-DERM® Clear by measuring 0.5 grams of OBAGI NU-DERM® BLENDER®, followed by a prescribed amount of tretinoin. Combine and apply evenly on the arm.

The patient performs the pre-treatment regimen in accordance with these instructions and preconditions the surface of skin in need of a skin cancer treatment for three weeks prior to the procedure.

Treatment:

A doctor then performs electrodessication and curettage as the skin cancer removal process. This electrodessication and curettage process is performed by procedures known in the art.

Example 2

A 35 year old white male in good general health is presented to dermatologist for removal of a small tumor from his face. The patient has little sun damage and indicates the desire to minimize, reduce, or eliminate the any side effects from the skin cancer treatment, especially scarring.

Pre-treatment:

The patient is started on a pre-treatment protocol to precondition his skin for upcoming skin cancer treatment.

The patient is prescribed tretinoin (0.05% or 0.1%) and provided with a pre-treatment kit containing a container of foaming gel, toner, OBAGI NU-DERM® Clear formulation, OBAGI NU-DERM® SUNFADER® formulation, OBAGI NU-DERM® BLENDER®, and prescribed tretinoin. Each container provides enough formulation in an amount sufficient to be applied to face as instructed below for between 3 to 6 weeks prior to the skin cancer treatment.

Each kit contains instructions for the patient to apply the pre-treatment compositions every morning. The instructions require the following steps to be followed in the morning in sequential order: 1) apply a nickel-sized amount of foaming gel to wet skin, massage into entire face and neck and rinse thoroughly; 2) apply toner using cotton pads or fingertips to entire face; 3) apply 0.5 grams of OBAGI NU-DERM® Clear to face; and 4) apply OBAGI NU-DERM® SUNFADER® to face and neck (Application of protective composition can be repeated after 2 hours if patient is in direct sunlight).

The instructions further require the following steps to be followed in the evening in sequential order: 1) apply a nickel-sized amount of foaming gel to wet skin, massage into entire face and neck and rinse thoroughly; 2) apply toner using cotton pads or fingertips to entire face; 3) apply 0.5 grams of OBAGI NU-DERM® Clear to face; 4) apply OBAGI NU-DERM® BLENDER® (0.5 grams) and tretinoin (0.5 grams). Apply in the evening after OBAGI NU-DERM® Clear by measuring 0.5 grams of OBAGI NU-DERM® BLENDER®, followed by a prescribed amount of tretinoin. Combine and apply evenly on entire face, extending to the hairline. Apply around eye area as directed.

The patient performs the pre-treatment regimen in accordance with these instructions and preconditions the surface of skin having the tumor and in need of a skin cancer treatment for three weeks prior to the skin cancer treatment.

Treatment:

A doctor then performs electrodessication and curettage as the skin cancer removal process. This electrodessication and curettage process is performed by procedures known in the art.

Post-treatment:

After re-epithelialization (approximately 10 days after the ED&C), the patient is started on a post-treatment protocol to help the skin heal quickly, and to reduce the likelihood of post-procedural reactions or complications.

The patient is prescribed tretinoin (0.05% or 0.1%) and provided with a post-treatment kit containing a container of gentle cleanser, toner, OBAGI NU-DERM® Clear formulation, OBAGI NU-DERM® SUNFADER® formulation, OBAGI NU-DERM® BLENDER®, and prescribed tretinoin. Each container provides enough formulation in an amount sufficient to be applied to face as instructed below for between 3 to 6 weeks after the skin cancer treatment.

Each kit contains instructions for the patient to apply the post-treatment compositions every morning. The instructions require the following steps to be followed in the morning in sequential order: 1) apply gentle cleanser to face, rinse with lukewarm water; 2) apply toner using fingertips to entire face (do not rinse); 3) apply 0.5 grams of OBAGI NU-DERM® Clear to face in feathering motion; and 4) apply OBAGI NU-DERM® SUNFADER® to face and neck. Application of protective composition can be repeated after 2 hours if patient is in direct sunlight.

Instructions further require the following steps to be followed in the evening in sequential order: 1) apply a nickel-sized amount of gentle cleanser to wet skin, massage into entire face and neck and rinse thoroughly; 2) apply toner using cotton pads or fingertips to entire face; 3) apply 0.5 grams of OBAGI NU-DERM® Clear to face; 4) apply OBAGI NU-DERM® BLENDERS (0.5 grams) and tretinoin (0.5 grams). Apply in the evening after OBAGI NU-DERM® Clear by measuring 0.5 grams of OBAGI NU-DERM® BLENDER®, followed by a prescribed amount of tretinoin. Combine and apply evenly on entire face, extending to the hairline. Apply around eye area as directed.

The patient performs the post-treatment regimen in accordance with these instructions and post-conditions the surface of skin subjected to a skin cancer treatment for three weeks after the procedure. The patient does not have adverse events such as reactions or complications.

Example 3

A study is conducted to evaluate pre- and post-treatment of sites of electrodessication and curettage therapy for nonmelanoma skin cancer on wound healing and scar cosmesis. Each subject follows a prescribed treatment regimen twice a day (in the morning and at night) for three weeks prior to the electrodessication and curettage procedure. The pre-treatment regimen involves applying the designated skin care product from the commercially available OBAGI NU-DERM® system in the smallest possible amount sufficient to cover the site intended for electrodessication and curettage therapy. The regimen is as follows:

|  | Morning | Evening |
| --- | --- | --- |
| Prepare | Foaming Gel | Foaming Gel |
|  | Toner | Toner |
| Correct | OBAGI NU-DERM ® Clear | OBAGI NU-DERM ® Clear |
|  | 4% Hydroquinone 1 gm | 4% Hydroquinone 1 gm |
| Stimulate |  | Tretinoin 0.05% |
|  |  | BLENDER ® 4% HQ 0.5 gm |
| Protect | SUNFADER ® |  |

For comparison, a control group uses the following pre-treatment regimen:

|  | Morning | Evening |
| --- | --- | --- |
| Prepare | Cetaphil ® Cleanser | Cetaphil ® Cleanser |
| Correct/Protect | Aquaphor ® healing ointment | Aquaphor ® healing ointment |

After three weeks, electrodessication and curettage are performed. For three weeks after the procedure, treatment is limited to application of Aquaphor® healing ointment and a bandage only. After sufficient re-epithelialization occurs to allow resumption of the study protocol, subjects resume treatment with the previously used treatment regimen. An assessment of wound cosmesis is periodically during the study.

While several embodiments of the disclosure have been described, it is not intended that the disclosure be limited thereto, as it is intended that the disclosure be as broad in scope as the art will allow and that the specification be read likewise. Therefore, the above description should not be construed as limiting, but merely as exemplifications of embodiments. Those skilled in the art will envision other modifications within the scope and spirit of the claims appended hereto.

What is claimed is:

1. A method comprising:
preconditioning an area of skin of a subject by sequential topical application of a preparatory composition and a corrective composition to the area of skin; and
performing a radiation or photodynamic therapy skin cancer treatment on the preconditioned area of skin whereby preconditioning the skin reduces side effects associated with the skin cancer treatment compared to skin that is not preconditioned for receiving a skin cancer treatment.

2. A method as in claim 1 further comprising applying a protective composition after application of the corrective composition.

3. A method as in claim 1 further comprising waiting a predetermined period of time and repeating the preconditioning.

4. A method comprising:
post-treating an area of skin of a subject that has previously been treated with a radiation or photodynamic therapy skin cancer treatment by sequential topical application of a preparatory composition and a corrective composition to the area of skin whereby post-treating the skin reduces side effects associated with the skin cancer treatment compared to skin that is not post-treated after receiving a skin cancer treatment.

5. A method as in claim 4 further comprising applying a protective composition after application of the corrective composition.

6. A method as in claim 4 further comprising waiting a predetermined period of time and repeating the post-treating.

7. A method comprising:
preconditioning an area of skin of the subject by administering to the area of skin a first treatment and, after a predetermined period of time, a second treatment,
the first treatment comprising the sequential topical application of one or more preparatory compositions, a first corrective composition, and one or more protective compositions;
the second treatment comprising the sequential topical application of one or more preparatory compositions, and a second corrective composition,
wherein the second corrective composition comprises a first active ingredient sensitive to oxidation and a retinoid; and
treating the skin with a radiation or photodynamic therapy skin cancer treatment whereby preconditioning the skin reduces side effects associated with the skin cancer treatment compared to skin that is not preconditioned for receiving a skin cancer treatment.

8. The method of claim 7 wherein the one or more preparatory compositions are selected from the group consisting of cleansers, toners and combinations thereof.

9. The method of claim 7 wherein the one or more protective compositions are selected from the group consisting of sunscreens, sun blocks, moisturizers and combinations thereof.

10. The method of claim 7 wherein the first corrective composition comprises an active ingredient that is sensitive to oxidation; a preservative; a chelating agent; an emulsifier; a humectant; a pH adjuster; an antioxidant; an emollient; a reducing agent and water.

11. The method of claim 7 wherein the first corrective composition comprises hydroquinone.

12. The method of claim 7 wherein the second corrective composition further comprises a preservative; a chelating agent; an emulsifier; a humectant; a pH adjuster; an antioxidant; an emollient; a reducing agent and water.

13. The method of claim 7 wherein the first active ingredient is hydroquinone.

14. The method of claim 7 further comprising the step of waiting at least four hours between the first treatment and the second treatment.

15. The method of claim 7 further comprising
post-treating the skin of the subject treated with a radiation or photodynamic skin cancer treatment by administering to the area of skin a first treatment and, after a predetermined period of time, a second treatment,
the first treatment comprising the sequential topical application of one or more preparatory compositions, a first corrective composition, and one or more protective compositions;
the second treatment comprising the sequential topical application of one or more preparatory compositions, and a second corrective composition,
wherein the second corrective composition comprises a first active ingredient sensitive to oxidation and tretinoin.

16. A method comprising:
preconditioning an area of skin of the subject by administering to the area of skin a first treatment and, after a predetermined period of time, a second treatment,
the first treatment comprising the sequential topical application of a cleanser, a toner, a first corrective composition containing hydroquinone, and a protective composition;
the second treatment comprising the sequential topical application of a cleanser, a toner, a second corrective composition comprising hydroquinone and a retinoid; and
performing a radiation or photodynamic therapy skin cancer treatment on the preconditioned area of skin whereby preconditioning the skin reduces side effects associated with the skin cancer treatment compared to skin that is not preconditioned for receiving a skin cancer treatment.

17. The method of claim 16 further comprising post-treating the area of skin subjected to the skin cancer treatment by administering to the area of skin a first treatment and, after a predetermined period of time, a second treatment,
the first treatment comprising sequential topical application of a cleanser, a toner, a first corrective composition containing hydroquinone, and a protective composition;
the second treatment comprising sequential topical application of a cleanser, a toner, a second corrective composition comprising hydroquinone and a retinoid.

18. The method of claim 16 wherein the first pre-conditioning treatment occurs in the morning.

19. The method of claim 18 wherein second pre-conditioning treatment occurs at least four hours after the first pre-conditioning treatment.

20. The method of claim 17 wherein the first post-treating treatment occurs in the morning.

21. The method of claim 20 wherein second post-treating treatment occurs at least four hours after the first post-treating treatment.

* * * * *